United States Patent
Veatch

(10) Patent No.: US 9,931,229 B2
(45) Date of Patent: Apr. 3, 2018

(54) GRIPPING DEVICE WITH SWITCHABLE PREHENSION MODES

(71) Applicant: Invisible Hand Enterprises, LLC, Westminster, CO (US)

(72) Inventor: Bradley Delton Veatch, Westminster, CO (US)

(73) Assignee: INVISIBLE HAND ENTERPRISES, LLC, Westminster, CO (US)

(*) Notice: Subject to any disclaimer, the term of this patent is extended or adjusted under 35 U.S.C. 154(b) by 0 days.

(21) Appl. No.: 15/632,375

(22) Filed: Jun. 25, 2017

(65) Prior Publication Data

US 2017/0290682 A1 Oct. 12, 2017

Related U.S. Application Data

(60) Division of application No. 15/275,436, filed on Sep. 25, 2016, now Pat. No. 9,737,418, which is a continuation of application No. 14/338,104, filed on Jul. 22, 2014, now Pat. No. 9,474,631.

(60) Provisional application No. 61/857,096, filed on Jul. 22, 2013.

(51) Int. Cl.
| | |
|---|---|
| A61F 2/58 | (2006.01) |
| A61F 2/68 | (2006.01) |
| A61F 2/76 | (2006.01) |
| A61F 2/50 | (2006.01) |
| A61F 2/74 | (2006.01) |
| A61F 2/70 | (2006.01) |

(52) U.S. Cl.
CPC .............. *A61F 2/588* (2013.01); *A61F 2/68* (2013.01); *A61F 2/76* (2013.01); *A61F 2002/503* (2013.01); *A61F 2002/5007* (2013.01); *A61F 2002/5038* (2013.01); *A61F 2002/5072* (2013.01); *A61F 2002/5093* (2013.01); *A61F 2002/704* (2013.01); *A61F 2002/74* (2013.01)

(58) Field of Classification Search
CPC .. A61F 2/58; A61F 2/583; A61F 2/586; A61F 2/588
See application file for complete search history.

(56) References Cited

U.S. PATENT DOCUMENTS

| | | |
|---|---|---|
| 1,423,296 A | 7/1922 | Francis |
| 1,608,689 A | 11/1926 | Frederick |
| 1,742,269 A | 1/1930 | McElroy |
| 2,285,885 A | 6/1942 | Becker |
| 2,364,313 A | 12/1944 | Pecorella |
| 2,549,074 A | 4/1951 | Meyer et al. |
| 4,685,924 A | 8/1987 | Massey |
| 4,685,929 A | 8/1987 | Monestier |
| 7,341,295 B1 | 3/2008 | Veatch et al. |
| 2014/0081425 A1 | 3/2014 | Sensinger |

*Primary Examiner* — Bruce E Snow
(74) *Attorney, Agent, or Firm* — IPAlternative, LLC

(57) ABSTRACT

The present invention is a switchable gripping terminal device that can be switched from a voluntary open prehension mode to a voluntary closed prehension mode, at will by the user. In an embodiment of the present invention, the terminal device may comprise a movable digit attached to a fixed digit, whereby the user can actuate the movable digit, such that the movable digit rotates relative to the fixed digit. The terminal device may comprise a lever, which enables the user to switch from a first mode, voluntary open (VO), to a second mode, voluntary closed (VC). This switchable biasing means, allows the user to decide the prehension mode, and easily switch the mode at will, according to the circumstances.

7 Claims, 8 Drawing Sheets

GRIPPING DEVICE WITH SWITCHABLE PREHENSION MODES

CROSS REFERENCE TO RELATION APPLICATION

The present application is a divisional application of U.S. Non-Provisional application Ser. No. 15/275,436 filed on Sep. 25, 2016, which is a continuation of U.S. Non-Provisional application Ser. No. 14/338,104 filed on Jul. 22, 2014, which claims the benefit of U.S. Provisional Application No. 61/857,096 filed Jul. 22, 2013, which are incorporated herein by reference in their entirety.

TECHNICAL FIELD

This invention relates generally to the field of prosthetics, more specifically to a terminal device with switchable prehension modes.

BACKGROUND OF DISCLOSURE

The following text should not be construed as an admission of knowledge in the prior art. Furthermore, citation or identification of any document in this application is not an admission that such document is available as prior art to the present invention, or that any reference forms a part of the common knowledge in the art.

In the field of prosthetics, many components are operated using power harvested from the user's own musculature using harnessing and a Bowden cable like those used for bicycle brakes and derailleurs. This form of operation is called body-powered, or BP. One such BP component is called a terminal device (TD) or gripper, and its function is to replace a missing hand for upper-limb amputees. It is a device that permits the user to grasp objects. Two configurations of TD are commonly used: voluntary-opening (VO), and voluntary-closing (VC).

With VO operation, the terminal device opens as the user increases their cable tension, due to an applied force. To grasp an object, they first apply a force to open the TD to larger than they require for the object, called sizing, or sizing the aperture, and then they move the TD around the object or bring the object between the grasping digits, hook structures, etc. Relaxing the cable tension allows the device to close and apply a prehension force to the object. This system behaves mechanically identical to a spring-loaded clamp.

Advantages of VO devices are that the TD will grasp an object even if the user allows the cable tension to vanish or go slack. This prevents muscle fatigue. The devices are very simple, and use replaceable rubber bands or springs to generate a prehension force. Drawbacks are that the prehension or pinch force maximum is set by the strength of the rubber bands. Many users add bands to generate a higher force, but then must modulate the cable tension to avoid crushing delicate objects. This requires muscular exertion to offset a portion of the pinch force, causing fatigue and over a period time secondary health consequences that can be debilitating and even devastating. Repetitive stress or overuse syndrome, cumulative traumatic injury, pain, loss of bodily function, and significant medical treatment costs are common, along with lost work.

However, if the user operates the cable such that it is rarely allowed to go slack, the user can develop a sense for how much pinch force they are applying. This ability to sense objects through the cable is called physiological proprioception. It is the same physiological connection that allows a tennis racket, golf club, bat, etc. to become an extension of the user's body; they know precisely where in space around their body the instrument is and are able to use it with extraordinary skill. Cable-operated, or BP terminal devices also preserve proprioception and this is one of the primary reasons they remain popular over more sophisticated technologies even today.

Voluntary-closing devices actuate in exactly the opposite manner. As the user increases their cable tension, the device closes to apply a prehension force. Advantages are the device preserves proprioception, and pinch force is proportional to the cable tension, due to the applied force, allowing the user to "feel" the object being grasped, and operation is more intuitive to the user. Maximum pinch force is determined by the user's strength, not elastic bands as with VO operation. Drawbacks of VC are that at rest, the TD is open, which can be awkward when it is not being used. Also, to sustain prehension, the user must sustain their cable tension, often resulting in fatigue or dropping objects if the user moves their torso and cable tension fluctuates. For general carrying or holding objects passively, VO is preferred, while dexterous tasks benefit from VC operation. Each mode has its applications and areas of performance where it excels.

The inventor is not aware of any mechanically simple TD designs that enable switching between modes. At least two reasons exist that have inhibited the development of a gripping device with a simple design for easily switching between prehension modes.

First, in VO, the TD is held closed with a strong spring force. In VC it must be held open with a weak or light force to avoid fatiguing the user. Changing positions of the moving digit from open to close while simultaneously changing the spring force is a difficult engineering problem. The present invention achieves two beginning states-one the "at rest" VO position with the digits closed and the second the "at rest" VC position with the digits open-using an over-the-center switching mechanism that changes the direction of the torque or moment about the moving digit's pivot as well as its magnitude. An innovative aspect of this mechanism is the use of a spatial mechanism; the over-the-center lever moves out of the plane in which the remaining mechanism operates.

Second, the device must change operating modes from VO to VC and back without changing the cable resting position. If the cable moves or suddenly gets tensioned or highly slack, the user will be unable to operate the device without having to adjust their harness. This is difficult for an amputee to achieve. Harness and cable settings are exquisitely sensitive to variation, minor changes can render the system unusable. This is one of the chief reasons upper-limb prosthetic fitting and adjustment is considered very difficult and an area of prosthetic expertise. This invention exploits geometric symmetry about the over-the-center switching mechanism that allows the initial starting cable excursion positions to be identical, thereby eliminating problems that arise when initial cable position changes.

The field of prosthetics has many examples of body-actuated gripping devices that are either VO or VC devices. Old and new examples abound in the patent literature. Examples of VO-only gripping devices include U.S. Pat. Nos. 1,608,689; 1,742,269; 2,285,885; 2,364,313; 4,685,924, all of which are incorporated by reference herein in their entireties. Examples of VC only gripping devices include U.S. Pat. Nos. 1,423,296; 2,549,074; 4,685,929, all of which are incorporated by reference herein in their entireties.

U.S. Pat. No. 7,341,295, which is incorporated by reference herein in its entirety, provides an example by the present inventor of a selectable voluntary opening/voluntary closing mechanism, whereby a single prehensor can be switched back and forth between a voluntary closing mode and a voluntary opening mode. However, this design is extremely complex.

Thus, it is clearly evident that there is a long felt need in the field of prosthetics for a body-actuated gripping device with an easily switchable prehension mode (from VO mode to VC mode and back again), that is also simple in design and operation, easy to manufacture, and economical from both a purchase price perspective and maintenance perspective.

SUMMARY OF DISCLOSURE

It is therefore an objective of this disclosure to describe a gripping device with a prehension mode that can be easily switched by an amputee from one mode of operation to the other and back again; e.g. from a voluntary open mode to a voluntary close mode, and from a voluntary close mode to a voluntary open mode.

It is a further objective of this disclosure to provide an easily switchable gripping device, wherein the cable resting position is the same regardless of whether the device is in VO mode, or in VC mode.

It is a further objective of this disclosure to provide a switchable gripping device, wherein when the device is in VC mode, the force needed to close the device is relatively low, while still providing a comparably strong closing force when switched to the VO mode.

It is a further objective of this disclosure to provide a gripping device with a switchable prehension mode of a simple mechanical design that is easy to operate by the user.

It is a further objective of this disclosure to provide a gripping device with a switchable prehension mode that, because of its simple design, is easy to manufacture, and is characterized by low manufacturing costs and maintenance costs.

An aspect of the present invention is a terminal device, comprising a movable digit, comprising a palmar side, a distal end, and a proximal end, wherein the distal end and the proximal end are aligned along a first axis, to form a distal half and a proximal half. The terminal device also comprises a fixed digit, comprising a dorsal side, a distal end, and a proximal end, wherein the distal end of the fixed digit and the proximal end of the fixed digit are aligned along a second axis, to form a distal half and a proximal half. The terminal device also comprises a connecting means, comprising a dorsal side, a palmar side, a distal side and a proximal side mounted on the proximal half of the fixed digit, and movably attached to the proximal half of the movable digit such that the movable digit can rotate relative to the fixed digit, such that when the first and second axis are substantially parallel, the palmar side of the movable digit faces the dorsal side of fixed digit. The terminal device also comprises a lever, comprising a first end, and a second end, such that the first end is movably attached near the connecting means to the movable digit, wherein the lever can be switched from a first position to a second position, wherein the first position is defined by the second end of the lever being positioned on the palmar side of the connecting means, and the second position is defined by the second end of the lever being positioned on the dorsal side the connecting means.

An aspect of the present invention is a switchable biasing means, wherein the switchable biasing means comprises a first position, wherein the movable digit is biased to an open position by a passive force generating means, until a user applies an active force generating means that is greater than the passive generating force, resulting in the movable digit moving to a closed position. When the user releases the active force generating means, the movable digit moves from the closed position back to the open position.

A further aspect of the present invention is a switchable biasing means further comprising a second position, wherein the movable digit is biased to a closed position by a passive force generating means, until a user applies an active force generating means that is greater than the passive generating force, resulting in the movable digit moving to an open position. When the user releases the active force generating means, the movable digit moves from open position back to the closed position.

An aspect of the present invention, is a terminal device as described above, further comprising a passive force generating means attached to the second end of the lever in a direction substantially towards the distal end of the fixed digit, and an active force generating means attached to the second end of the lever in a direction substantially towards the proximal end of the fixed digit, wherein the active force generating means is an actuating mechanism. When the lever is in the first position and the actuating mechanism applies the active force, and the active force is greater than the passive force, the lever is pulled from the distal side of the connecting means to the proximal side of the first connecting means, thereby moving the distal end of the movable digit towards the distal end of the fixed digit from an open position to a closed position. When the lever is in the second position and the actuating mechanism applies the active force, and the active force is greater than the passive force, the lever is pulled from the distal side of the connecting means to the proximal side of the connecting means, thereby moving the distal end of the movable digit away from the distal end of the fixed digit from the closed position to the open position.

One having skill in the art will appreciate that embodiments of the present disclosure may have various sizes, shapes and physical dimensions. The sizes of the various elements of embodiments of the present disclosure may be sized based on various factors including, for example, engineering specifications of components used to construct the device, the anatomy of the user, the person or other device operating with or otherwise using the device, and the limb being fitted or replaced.

One having skill in the art will appreciate that embodiments of the present disclosure may be constructed of materials known to provide, or predictably manufactured to provide, the various aspects of the present disclosure. These materials may include, for example, stainless steel, titanium alloy, aluminum alloy, chromium alloy, and other metals or metal alloys. These materials may also include, for example, PEEK, carbon fiber, ABS plastic, polyurethane, resins, particularly fiber-encased resinous materials rubber, latex, synthetic rubber, synthetic materials, polymers, and natural materials.

One having skill in the art will appreciate that embodiments of the present disclosure may be used in conjunction with devices that employ automated or semi-automated manipulation. Embodiments of the present disclosure may be designed such that the device may be used and manipulated and/or actuated, for example, remotely by an operator, remotely by an operator through a computer controller, by an operator using proportioning devices, programmatically by a computer controller, by servo-controlled mechanisms, by hydraulically-driven mechanisms, by pneumatically-driven mechanisms or by piezoelectric actuators.

One embodiment of the present invention is a switchable prehension terminal device comprising a first digit having a distal end and a proximal end; a second digit rotatably connected to the first digit via a first connecting means, wherein the first connecting means comprises a dorsal side and a palmar side; a biasing means operatively connected to the second digit via a second connection means; a passive force generating means attached to the biasing means in a direction substantially towards the distal end of the first digit; an active force generating means attached to the biasing means in a direction substantially towards the proximal end of the first digit; and wherein the biasing means is movable between a first position and a second position, wherein the first position is defined by the biasing means positioning the passive force and active force means on the palmar side of the first connecting means, and the second position is defined by the biasing means positioning the passive force and active force means on the dorsal side of the first connecting means.

Another embodiment of the present invention is a method of using a switchable prehension terminal device providing a first digit having a distal end and a proximal end; providing a second digit rotatably connected to the first digit via a first connecting means, wherein the first connecting means comprises a dorsal side and a palmar side; providing a biasing means operatively connected to the second digit via a second connection means; providing a passive force generating means attached to the biasing means in a direction substantially towards the distal end of the first digit; providing an active force generating means attached to the biasing means in a direction substantially towards the proximal end of the first digit, wherein the biasing means positions the passive force and active force means on the palmar side of the first connecting means; placing an object between the first digit and the second digit; engaging the active force means to provide a force greater than the passive force means such that the second digit rotates to secure the object between the first digit and the second digit.

Yet another embodiment of the present invention is a method of using a switchable prehension terminal device comprising providing a first digit having a distal end and a proximal end; providing a second digit rotatably connected to the first digit via a first connecting means, wherein the first connecting means comprises a dorsal side and a palmar side; providing a biasing means operatively connected to the second digit via a second connection means; providing a passive force generating means attached to the biasing means in a direction substantially towards the distal end of the first digit; providing an active force generating means attached to the biasing means in a direction substantially towards the proximal end of the first digit, wherein the biasing means positions the passive force and active force means on the dorsal side of the first connecting means; engaging the active force means to provide a force greater than the passive force means; placing an object between the first digit and the second digit; disengaging the active force means to provide a force less than the passive force means such that the passive force means rotates the second digit to secure the object between the first digit and the second digit.

This Summary of the Invention is neither intended nor should it be construed as being representative of the full extent and scope of this disclosure. Moreover, references made herein to "the present disclosure" or aspects thereof, should be understood to mean certain embodiments and should not necessarily be construed as limiting all embodiments to a particular description. The present invention is set forth in various levels of detail in the Summary of the Disclosure as well as in the attached drawings and the Description of Embodiments and no limitation as to the scope is intended by either the inclusion or non-inclusion of elements, components, etc. in this Summary of the Disclosure. Additional aspects will become more readily apparent from the Description of Embodiments, particularly when taken together with the drawings.

BRIEF DESCRIPTION OF DRAWINGS

The accompanying drawings are incorporated into and form a part of the specification to illustrate examples of how the aspects, embodiments, or configurations can be made and used and are not to be construed as limiting the aspects, embodiments, or configurations to only the illustrated and described examples. Further features and advantages will become apparent from the following, more detailed, description of the various aspects, embodiments, or configurations.

REFERENCE NUMERALS

Figure 1:
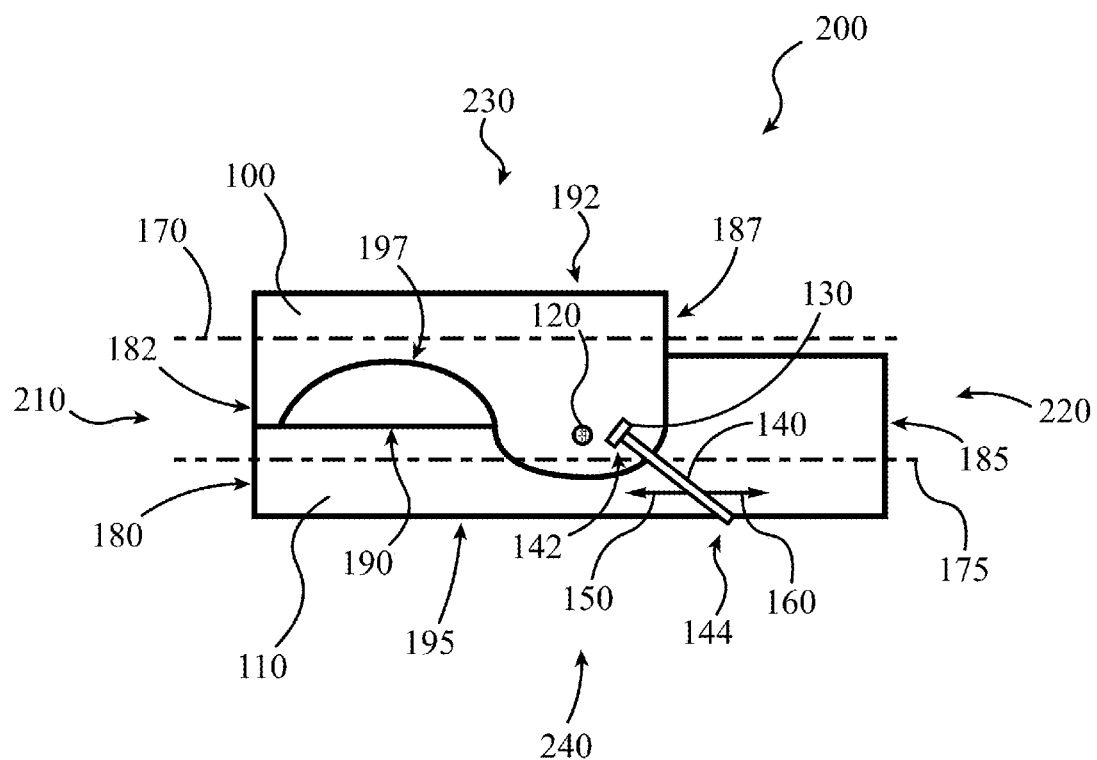
FIG. 1 illustrates an embodiment of the present invention, a switchable prehensor in voluntary closed mode, in the closed position.

100—movable digit
110—fixed digit
120—first connecting means
122—dorsal side of first connecting means
124—palmar side of first connecting means
126—distal side of first connecting means
128—proximal side of first connecting means
130—second connecting means
140—lever
142—first end of lever
144—second end of lever
150—passive force generating means
160—active force generating means
170—first axis
175—second axis
180—distal end of fixed digit
182—distal end of movable digit
185—proximal end of fixed digit
187—proximal end of movable digit
190—dorsal side of fixed digit 192—dorsal side of movable digit
195—palmar side of fixed digit
197—palmar side of movable digit
200—terminal device
210—distal end of terminal device
220—proximal end of terminal device
230—dorsal side of terminal device
240—palmar side of terminal device
500—tension cord
510—cable
520—tension cord guide
530—cable guide
540—voluntary open stop (VO stop)
550—voluntary close stop (VC stop)
560—lever guide
570—tension cord anchor
580—flag
590—LVC (length)
600—LVO (length)

DESCRIPTION OF EMBODIMENTS

The following detailed description illustrates the invention by way of example and not by way of limitation. This description will clearly enable one skilled in the art to make and use the invention.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

An aspect of the present invention is a terminal device, comprising a movable digit, comprising a palmar side, a distal end, and a proximal end, wherein the distal end and the proximal end are aligned along a first axis, to form a distal half and a proximal half. The terminal device also comprises a fixed digit, comprising a dorsal side, a distal end, and a proximal end, wherein the distal end of the fixed digit and the proximal end of the fixed digit are aligned along a second axis, to form a distal half and a proximal half. The terminal device also comprises a connecting means, comprising a dorsal side and a palmar side, mounted on the proximal half of the fixed digit, and movably attached to the proximal half of the movable digit such that the movable digit can rotate relative to the fixed digit, such that when the first and second axis are substantially parallel, the palmar side of the movable digit faces the dorsal side of fixed digit. The terminal device also comprises a lever, comprising a first end, and second end, such that the first end is movably attached near the connecting means to the movable digit, wherein the lever can be switched from a first position to a second position, wherein the first position is defined by the second end of the lever being positioned on the palmar side of the connecting means, and the second position is defined by the second end of the lever being positioned on the dorsal side the connecting means.

As used herein, the term "terminal device" refers to a gripping device or a prosthetic device, wherein such a device comprises one or more digits suitable for grasping, gripping, grabbing, holding, or performing other actions commonly performed by one or more fingers or a hand. As used herein, the term "digit" is synonymous with lever, phalange, and phalanx, or a joined collection of phalangeal segments constituting a grasping member or finger. A digit may comprise a relatively flat, planar structure, with just sufficient thickness to provide structural and mechanical support. Alternatively, a digit may comprise three dimensions that are roughly proportional to a natural human finger.

FIG. 1 illustrates one embodiment of the present invention, a terminal device 200, which may comprise a movable digit 100, movably connected to a fixed digit 110 by a first connecting means 120. The movable digit 100 may comprise a simple lever, or it may alternatively be a complicated anthropomorphic representation of a human finger. The movable digit 100 may comprise one or more joints. The movable digit 100 may comprise an outer layer that imitates the look, texture and/or feel of skin. The movable digit 100 may comprise a shape that facilitates gripping, grabbing, holding or grasping an article. For example, the movable digit 100 may comprise a palmar side 197 that has been fabricated to take the shape of an arc to form a gap between the palmar side 197 of the movable digit 100 and the dorsal side 190 of the fixed digit 110, even when the terminal device 200 is in a closed position, as shown in FIG. 1. Alternatively, there may be no gap between the movable digit 100 and the fixed digit 110 when the terminal device 200 is in the closed position. Alternatively, there may be some other geometrically shaped gap created in the movable digit 100, other than an arc, that forms a gap between the fixed digit 110 and the movable digit 100, when the terminal device 200 is in the closed position.

The fixed digit 110 may comprise a simple lever, or it may alternatively be a complicated anthropomorphic representation of a human finger. The fixed digit 110 may comprise one or more joints. The fixed digit 110 may comprise an outer layer that imitates the look, texture and/or feel of skin. The fixed digit 110 may comprise a shape that facilitates gripping, grabbing or grasping an article. For example, the fixed digit 110 may comprise a dorsal side 190 that has been fabricated to take the shape of an arc to form a gap between the palmar side 197 of the movable digit 100 and the dorsal side 190 of the fixed digit 110, even when the terminal device 200 is in a closed position. Alternatively, there may be no gap between the movable digit 100 and the fixed digit 110 when the terminal device 200 is in the closed position. Alternatively, there may be some other geometrically shaped gap created in the fixed digit 110, other than an arc, that forms a gap between the fixed digit 110 and the movable digit 100, when the terminal device 200 is in the closed position.

In some embodiments of the present invention, the distal ends (180 and 182) of the fixed digit 110 and the movable digit 100 may further comprise a shape adapted to help facilitate easier gripping, grasping or grabbing of an object such as a pencil, a glass, a tool or some other specific device for a specific task. For example, the movable digit 100, the fixed digit 110, or both may be provided with a groove or notch configured to receive a writing utensil.

Figure 2:
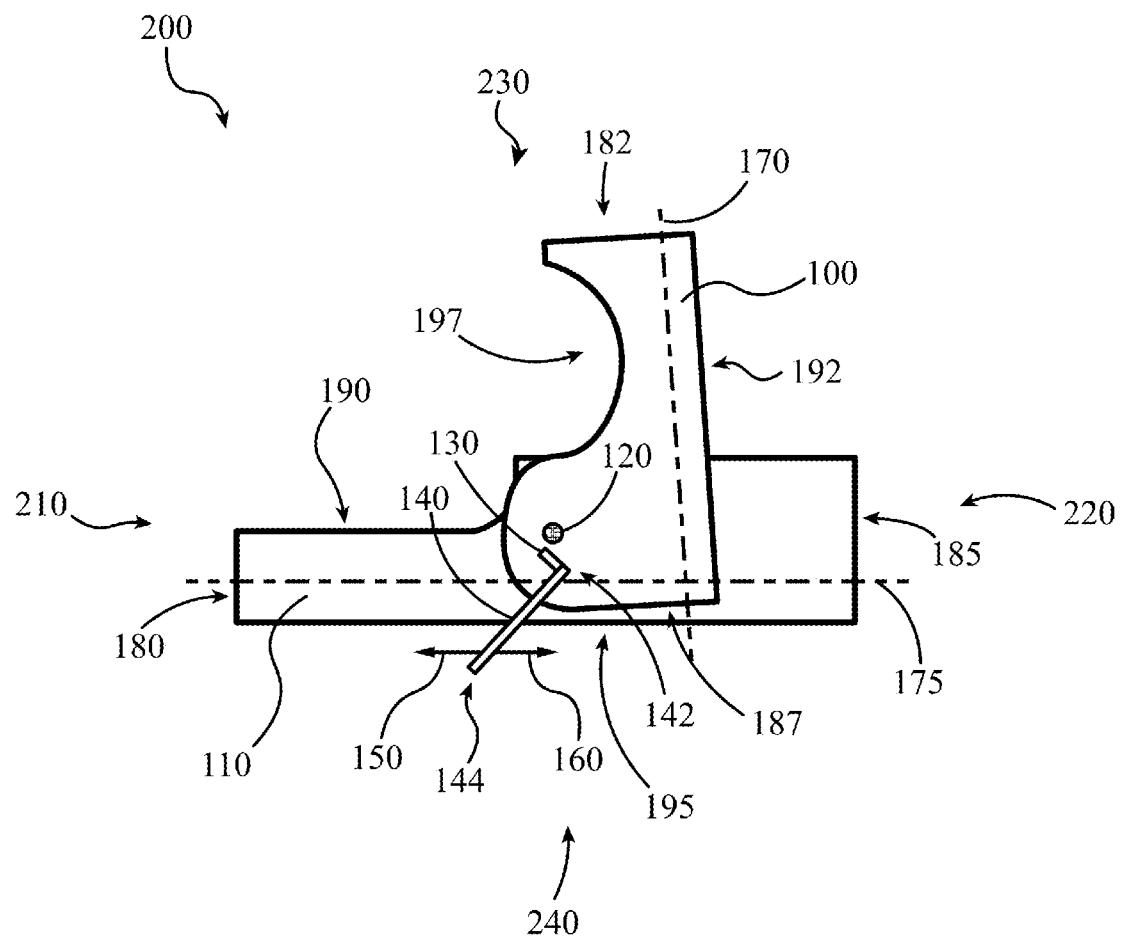
FIG. 2 illustrates an embodiment of the present invention, a switchable prehensor in voluntary closed mode, in the open position.

Referring again to FIG. 1, in some embodiments of the present invention, the first connecting means 120 mechanically connects the movable digit 100 to the fixed digit 110, such that the movable digit 100 may rotate around the first connecting means 120. This may be visualized by an axis (not shown) extending out of FIG. 1, perpendicular to the page from the first connecting means 120 (illustrated as a small round black circle), wherein the movable digit 100 rotates around this perpendicular axis. Referring to FIG. 2, movable digit 100 is shown in an open position after it has rotated roughly 90 degrees relative to the closed position shown in FIG. 1.

FIGS. 1 and 2 illustrate that the movable digit 100 and the fixed digit 110 may comprise an aspect ratio similar to that normal for human fingers. This depends upon the overall size of the terminal device 200 which may vary depending on whom it is fitted for; e.g. children, versus small adults, versus large adults. In some embodiments, the movable digit 100 and the fixed digit 110 may describe an aspect ratio significantly different from that normal for human fingers.

The movement of the movable digit 100 describes an arc created by the sweep of the distal tip around its point of rotation, the first connecting means 120. This arc is referred to as the angle of rotation. In some embodiments of the present invention, angle of rotation may range from about 10° to about 180°. In some embodiments of the present invention, angle of rotation may range from about 30° to about 160°. In some embodiments of the present invention, angle of rotation may range from about 50° to about 140°. The preferred angle of rotation between fixed and moving digits 110, 100 is between 60° and 120°, with an optimal angle of rotation of about 80°.

Both the movable digit 100 and the fixed digit 110 may describe a certain length defined by a first axis 170 for the movable digit 100 and a second axis 175 for the fixed axis (shown in FIGS. 1 and 2). In some embodiments of the present invention, the first axis 170 and the second axis 175 may be substantially parallel when the terminal device 200 is in a closed position. In some embodiments of the present invention, the first axis 170 and the second axis 175 may be substantially perpendicular when the terminal device 200 is in the open position. In some embodiments of the present invention, the movable digit 100 may pass through an angle of rotation comprising from about 10° to about 180° when moved from a closed position to an open position. In some embodiments of the present invention, the movable digit 100 may pass through an angle of rotation comprising from about 30° to about 160° when moved from a closed position to an open position. In some embodiments of the present invention, the movable digit 100 may pass through an angle of rotation comprising from about 50° to about 140° when moved from a closed position to an open position. In preferred embodiments of the present invention, the movable digit 100 may pass through an angle of rotation comprising from about 60° to about 120° when moved from a closed position to an open position. In an optimum embodiment, the movable digit 100 passes through an angle of rotation comprising about 80°.

In some embodiments of the present invention, the first connecting means 120 may comprise a cylindrical structure, selected from the group consisting of a pin, a nail, a screw, a rod, a rivet, and a circular section of cord tied into a loop. The first connecting means 120 may also be a largely cylindrical feature on either the movable digit 100 or fixed digit 110 that moves rotatably within a ring or annular structure on the opposing digit. The first connecting means 120 may also be a rounded "peninsular" tab located on either the moving digit 110 or the fixed digit 110 that rotates through a limited but adequate angle within the opposing digit.

Referring to FIGS. 1-2, an aspect of the present invention is a switchable biasing means, wherein the switchable biasing means comprises a first position, wherein the movable digit 100 is biased to an open position by a passive force generated by a passive force generating means 150, until a user applies an active force applied by an active force generating means 160 that is greater than the passive force, resulting in the movable digit 100 moving to a closed position as shown in FIG. 1. When the user releases the active force generating means 160, the movable digit 100 moves from the closed position back to the open position due to the passive force applied by the passive force generating means 150. In an embodiment of the present invention, the switchable biasing means may comprise a lever 140 attached to the movable digit 100 by a second connecting means 130, as shown in FIGS. 1-4. The passive force generating means 150 and the active force generating means 160 may both be attached to a second end 144 of the lever 140, but in opposing directions. The active force generating means 160 may apply an active force that pulls the lever 140 towards the proximal end 185 of the fixed digit 110. The passive force generating means 150 may apply a passive force that pulls the lever 140 towards the distal end 180 of the fixed digit 110.

Figure 3:
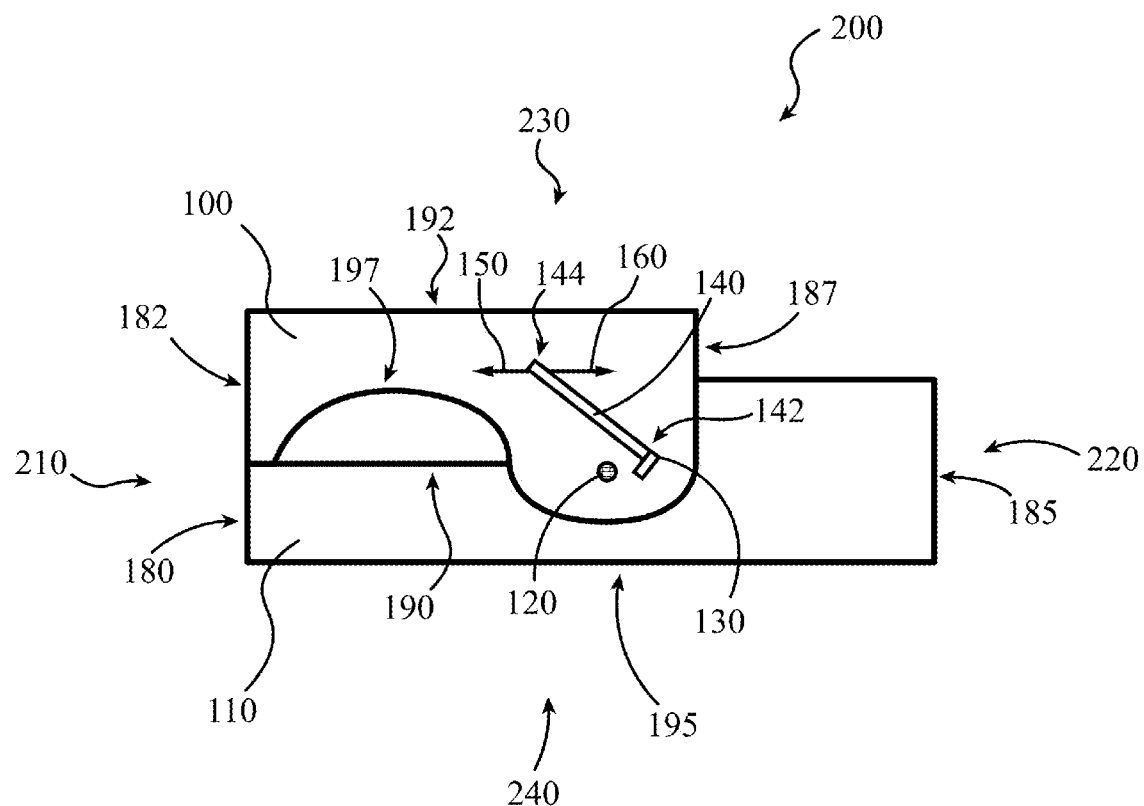
FIG. 3 illustrates an embodiment of the present invention, a switchable prehensor in voluntary open mode, in the closed position.
Figure 4:
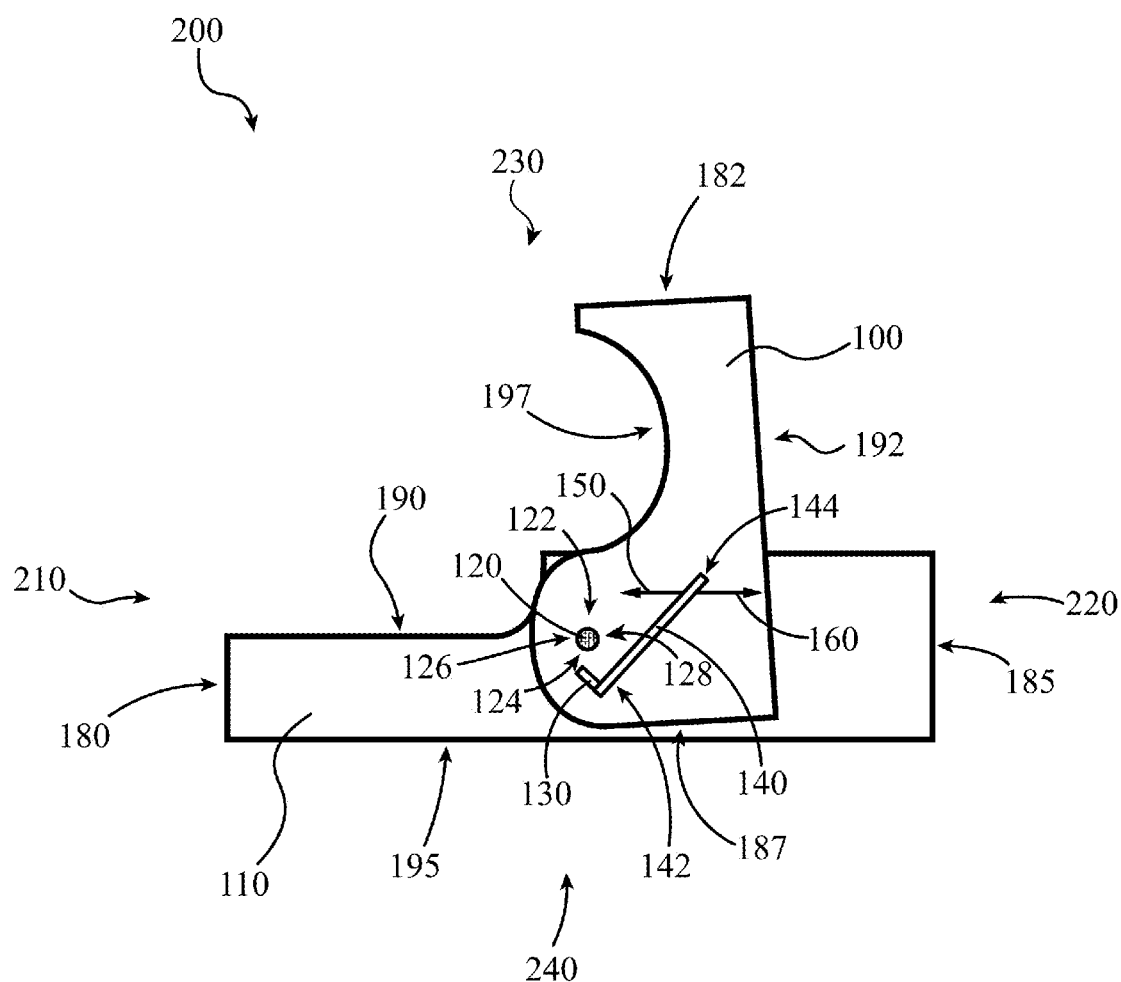
FIG. 4 illustrates an embodiment of the present invention, a switchable prehensor in voluntary open mode, in the open position.

Referring to FIG. 3-4, a further aspect of the present invention is a switchable biasing means further comprising a second position, wherein the movable digit 100 is biased to a closed position by a passive force generated by a passive force generating means 150, until a user applies an active force applied by an active force generating means 160 that is greater than the passive force, resulting in the movable digit 100 moving to an open position as shown in FIG. 4. When the user releases the active force generating means 160, the movable digit 100 moves from the open position back to the closed position due to the passive force applied by the passive force generating means 150. In some embodiments of the present invention, the switchable biasing means may comprise a lever 140 attached to the movable digit 100 by a second connecting means 130, as shown in FIGS. 1-4. The passive force generating means 150 and the active force generating means 160 may both be attached to a second end 144 of the lever 140, but in opposing directions. The active force generating means 160 may apply an active force that pulls the lever 140 towards the proximal end 185 of the fixed digit 110. The passive force generating means 150 may apply a passive force that pulls the lever 140 towards the distal end 180 of the fixed digit 110.

Referring again to FIGS. 1-4, in some embodiments of the present invention, the switchable biasing means may comprise a lever 140, wherein the first end 142 of the lever 140 may be movably attached to the second connecting means 130, wherein the second connecting means 130 may be positioned at or proximal to the first connecting means 120, on an axis that may be substantially parallel to the second axis 175. In some embodiments of the present invention, the second connecting means 130 and the second end 144 of the lever 140 may be positioned distal to the first connecting means 120. In some embodiments of the present invention, the second connecting means 130 and the second end 144 of the lever 140 may be positioned substantially adjacent to the first connecting means 120.

Referring to FIGS. 1-2, in some embodiments of the present invention, the lever 140, acting as a switchable biasing means, may comprise a first position wherein the second end 144 of the lever 140 may be positioned below the first connecting means 120, or towards the palmar side 240 of the terminal device 200. Further, while the lever 140 is in the first position, the second end 144 of the lever 140 may have a passive force generating means 150 attached to it, and an active force generating means 160, wherein the two apply forces that act in opposite directions, both substantially parallel to the second axis 175 (of the fixed digit 110). Further, while the second end 144 of the lever 140 is in the first position, located on the palmar side 124 of the first connection means 120, when the passive force generating means 150 is generating a passive force larger than the active force generated by the active force generating means 160, the second end 144 of the lever 140 may be pulled by the passive force generated by the passive force generating means 150 towards the distal end 180 of the fixed digit 110, such that the movable digit 100, which is attached to the lever 140 by the second connecting means 130 may be rotated to an open position as shown in FIG. 2. Alternatively, when the active force generated by the active force generating means 160 exceeds the passive force of the passive force generating means 150, the second end 144 of the lever 140 may be pulled by the active force generated by the active force generating means 160 towards the proximal end 185 of the fixed digit 110, such that the movable digit 100, may be rotated from the open position to the closed position as shown in FIG. 1.

Referring to FIGS. 3-4, in some embodiments of the present invention, the lever 140, acting as a switchable biasing means, may further comprise a second position wherein the second end 144 of the lever 140 may be positioned above the first connecting means 120, or towards the dorsal side 230 of the terminal device 200. Further, while the lever 140 is in the second position, the second end 144 of the lever 140 may have a passive force generating means 150 attached to it, and an active force generating means 160, wherein the two apply forces that act in opposite directions, both substantially parallel to the second axis 175 (of the fixed digit 110). Further, while the second end 144 of the lever 140 is in the second position, located on the dorsal side 122 of the first connection means 120, when the passive force generating means 150 is generating a passive force larger than the active force generated by the active force generating means 160, the second end 144 of the lever 140 may be pulled by the passive force generated by the passive force generating means 150 towards the distal end 180 of the fixed digit 110, such that the movable digit 100, which is attached to the lever 140 by the second connecting means 130 may be rotated to a closed position as shown in FIG. 3. Alternatively, when the active force generated by the active force generating means 160 exceeds the passive force of the passive force generating means 150, the second end 144 of the lever 140 may be pulled by the active force generated by the active force generating means 160 towards the proximal end 185 of the fixed digit 110, such that the movable digit 100, may be rotated from the closed position to the open position as shown in FIG. 4.

Referring again to FIG. 1, in some embodiments of the present invention, when the lever 140 is in the first position (directed towards the palmar side 240 of the terminal device 200) and when the passive force generated by the passive force generating means 150 is less than the active force generated by the active force generating means 160, and the terminal device 200 is in the closed position, the lever 140 may be oriented at an angle, hereinafter referred to as the "total swing angle", of about 45° from the second axis 175 (of the fixed digit 110), wherein the reference point for 0° from the second axis 175 is parallel with the second axis 175 and directed in the proximal direction, and 90° is perpendicular to the second axis 175 in the palmar direction. In some embodiments of the present invention, the lever 140 may be oriented at an angle between about 0° and about 180° from the second axis 175. In some embodiments of the present invention, the lever 140 may be oriented at an angle between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

In some embodiments of the present invention, the total swing angle is about 30°, about 40°, about 50°, about 60°, about 70°, about 80°, about 90°, about 100°, about 110°, about 120°, about 130°, about 140°, about 150°, about 160°, about 170°, or about 180°.

Referring again to FIG. 2, in some embodiments of the present invention, when the lever 140 is in the first position (directed towards the palmar side 240 of the terminal device 200) and when the passive force generated by the passive force generating means 150 is larger than the active force generated by the active force generating means 160, and the terminal device 200 is in the open position, the lever 140 may be oriented at a total swing angle of about 45° from the second axis 175 (of the fixed digit 110), wherein the reference point for 0° from the second axis 175 is parallel with the second axis 175 and directed in the distal direction, and 90° is perpendicular to the second axis 175 in the palmar direction. In some embodiments of the present invention, the lever 140 may be oriented at a total swing angle of between about 0° and about 180° from the second axis 175. In some embodiments of the present invention, the lever 140 may be oriented at a total swing angle of between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

Referring again to FIG. 3, in some embodiments of the present invention, when the lever 140 is in the second position (directed towards the dorsal side 230 of the terminal device 200) and when the passive force generated by the passive force generating means 150 is greater than the active force generated by the active force generating means 160, and the terminal device 200 is in the closed position, the lever 140 may oriented at a total swing angle of about 45° from the second axis 175 (of the fixed digit 110), wherein the reference point for 0° from the second axis 175 is parallel with the second axis 175 and directed in the distal direction, and 90° is perpendicular to the second axis 175 in the dorsal direction. In some embodiments of the present invention, the lever 140 may be oriented at a total swing angle between about 0° and about 180° from the second axis 175. In some embodiments of the present invention, the lever 140 may be oriented at a total swing angle between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

Referring again to FIG. 4, in some embodiments of the present invention, when the lever 140 is in the second position (directed towards the dorsal side 230 of the terminal device 200) and when the passive force generated by the passive force generating means 150 is less than the active force generated by the active force generating means 160, and the terminal device 200 is in the open position, the lever 140 may oriented at a total swing angle of about 45° from the second axis 175 (of the fixed digit 110), wherein the reference point for 0° from the second axis 175 is parallel with the second axis 175 and directed in the proximal direction, and 90° is perpendicular to the second axis 175 in the dorsal direction. In some embodiments of the present invention, the lever 140 may be oriented at a total swing angle between about 0° and about 180° from the second axis 175. In some embodiments of the present invention, the lever 140 may be oriented at a total swing angle between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

In some embodiments of the present invention, the second connecting means 130 may comprise a cylindrical structure, selected from the group consisting of a pin, a nail, a screw, a rod, and a rivet. In some embodiments of the present invention, the second connecting means 130 may be directly connected to the first connecting means 120. In some embodiments of the present invention, the second connecting means 130 may be separated from the first connecting means 120.

In some embodiments of the present invention, the lever 140 may be switched from a first position to a second position, and from a second position to a first position, by rotating the lever 140 relative to an axis defined by the second connecting means 130, in a plane that is substantially perpendicular to the first axis 170 and the second axis 175.

An aspect of the present invention, is a terminal device 200 as described above, further comprising a passive force generating means 150 attached to the second end 144 of the lever 140 for generating a passive force in a direction substantially towards the distal end 180 of the fixed digit 110, and an active force generating means 160 attached to the second end 144 of the lever 140 for generating an active force in a direction substantially towards the proximal end 185 of the fixed digit 110, wherein the active force generating means 160 is an actuating mechanism. When the lever 140 is in the first position and the actuating mechanism applies the active force, and the active force is greater than the passive force, the lever 140 is pulled from the distal side 126 of the first connecting means to the proximal side 128 of the first connecting means 120, thereby moving the distal end 182 of the movable digit 100 towards the distal end 180 of the fixed digit 110 from an open position to a closed position. When the lever 140 is in the second position and the actuating mechanism applies the active force, and the active force is greater than the passive force, the lever 140 is pulled from the distal side 126 of the first connecting means 120 to the proximal side 128 of the first connecting means 120, thereby moving the distal end 182 of the movable digit 100 away from the distal end 180 of the fixed digit 110 from the closed position to the open position. In some embodiments of the present invention, the passive force applied by the passive force generating means 150 and the active force applied by the active force generating means 160 are in substantially opposite directions. The passive force generated by the passive force generating means 150 may be in a direction substantially parallel with a longitudinal axis formed by the fixed digit 110, and may be directed towards the distal end 180 of the fixed digit 110. The active force generated by the active force generating means 160 may be in a direction substantially parallel with a longitudinal axis formed by the fixed digit 110, and may be directed towards the proximal end of the fixed digit 110.

In some embodiments of the present invention, the passive force generating means 150 may be selected from the group consisting of a spring, an elastic cord, a pressurized cylinder, and any other suitable stretchable member capable of storing mechanical energy. A spring may be selected from the groups consisting of extension, compression, torsion, clock, power, and constant force springs. Materials of construction may be selected as needed, depending on specific design criteria, these selections being known to those skilled in the art. Examples of materials of construction for springs include, but are not limited to, plastic and metal. Examples of materials of construction for elastic cords include, but are not limited to, plastic materials, elastic materials, and silastic materials. Rope, cord, and fibers may also be selected as appropriate for a specific design need. In general, the passive force generating means 150 is a mechanical element comprising an elastic component that can be either stretched and/or compressed from a first state in which the mechanical element has zero stored mechanical energy, to a second state wherein the mechanical element contains stored mechanical energy.

The stored energy acts as the passive force that moves the movable digit 100 back to a static equilibrium state, once the passive force exceeds the active force. It is an aspect of this invention to provide for adjustment of the magnitude of this passive biasing force. This can be accomplished by changing the attachment point on the lever 140 to effectively alter the lever length, changing where the passive force generating element is anchored, or by changing the internal force generating characteristics of the passive force generating element itself, for example increasing or decreasing the force generated by changing internal spring force, working fluid pressure, or other relevant characteristic applicable to the force generating device used.

Pull devices may include elastomer elements such as bungee cord and rubber bands, tension springs, and mechanical arrangements incorporating constant-force or power (i.e. "clock") springs. Other pull devices may include pneumatic and hydraulic devices, McKibben actuators, solenoids and electromagnetic devices, and reactive materials configured to provide a pulling or tensile force.

Pushing devices may include compression springs configured within a "piston"-like arrangement similar to vehicle shock absorbers or the telescoping tube used to support and retain toilet paper rolls in a dispenser. The devices listed for pull previously may also be configured to act on another rigid member that in turn provides a push force, effectively converting them to push devices.

In some embodiments of the present invention, the active force generating means 160 may be selected from the group consisting of a rope, cord, fiber, wire, filament, and any other flexible cord-like member. Unlike the passive force generating means 150, the active force generating means 160 may not have the ability to store energy. The active force generating means 160 may be essentially inelastic. This is because, for efficient operation, body movements used to activate the prosthetic terminal device 200 should translate into actual displacement of the device, not stretching of the control line, wire, or cable. Otherwise, the user may need to make excessive or unnatural movement to compensate for the inefficiencies of the system. In other embodiments, the active force generating means 160 may comprise an elastic component. Forces generated by the user are not the only active actuation forces that may be used. Others include hydraulic, pneumatic, electromechanical, active materials such as piezoelectric devices, reactive polymers, and magnetostrictive devices, as well as combinations of these means.

In some embodiments of the present invention, the ratio of a passive force applied to the lever 140 while the terminal device is open during VC mode, to a passive force applied to the lever 140 while the terminal device is closed during VO mode is about equal to one. Hereinafter, this ratio is referred to as the VCNO force ratio. In some embodiments of the present invention, the VCNO force ratio is less than about one. In some embodiments of the present invention, the VCNO force ratio is about 1.0, about 0.9, about 0.8, about 0.7, about 0.6, about 0.5, about 0.4, about 0.3, about 0.2, or about 0.1. In some embodiments of the present invention, the VCNO force ratio is greater than about one. In some embodiments of the present invention, the VCNO force ratio is about 1.0, about 1.1, about 1.2, about 1.3, about 1.4, about 1.5, about 1.6, about 1.7, about 1.8, about 1.9, or about 2.0. Assuming the lever length does not change, the VO passive force should generally be larger than VC passive force to generate useful pinch force.

In some embodiments of the present invention, the VC passive force at its lowest setting may generate from about 2 $lb_f$ to about 5 $lb_f$ of cable tension to ensure the user preserves physiological proprioception and the cable does not go slack, and to pull the control cable back through the housing so the device can be cycled and not "stuck" by cable drag. In some embodiments of the present invention, the VO passive force at its lowest setting may be selected to ensure that the TD closes fully, and maintaining the maximum VO passive force possible, while still allowing the user to operate and cycle the device.

A desired VCNO force ratio may be achieved by varying the elasticity of the means for providing a passive force, varying the length of the lever 140, the position of the proximal end of the lever 140 relative to the second axis 175, and the position of the proximal end of the lever 140 on the palmar-dorsal axis perpendicular to the second axis 175. In some embodiments of the present invention, VO>VC>about 2 $lb_f$ to about 5 $lb_f$ cable tension.

The invention has been described with reference to various specific and preferred embodiments and techniques. However, it should be understood that many variations and modifications may be made while remaining within the spirit and scope of the invention.

It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any sub-combination.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

Example 1

Figure 5:
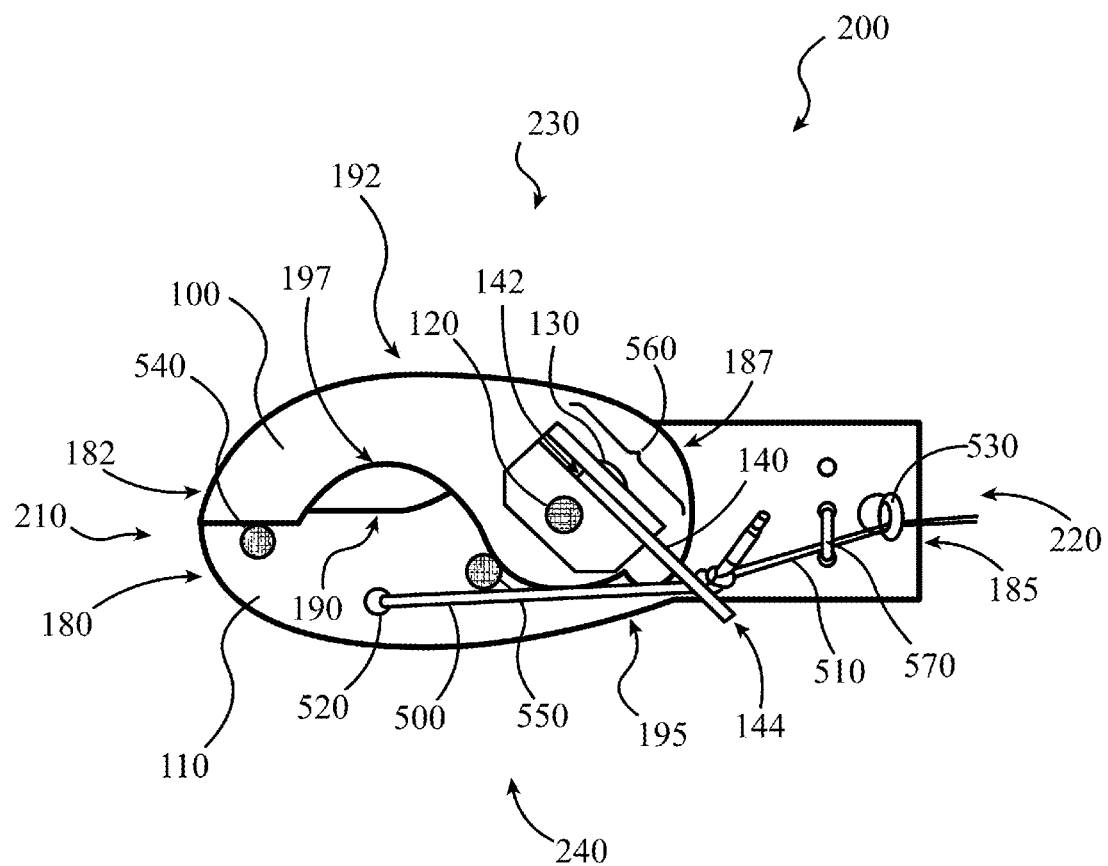
FIG. 5 illustrates an embodiment of the present invention, a reduction to practice of a switchable prehensor in voluntary closed mode, in the closed position.

An example of an actual reduction to practice of the present invention is shown in FIGS. 5-8. Referring first to FIG. 5, this switchable gripping device prototype is shown in the voluntary closed mode, in the closed position, wherein the user has pulled on the cable 510 to consciously pull the distal end 182 of the movable digit 100 towards the distal end 180 of fixed digit 110. FIG. 5 illustrates where the terminal device 200 is in the completely closed position. The final closed position in this prototype is limited by a VO stop 540. As long as the user continues to apply a sustained force to the cable 510, this force will be transferred to the lever 140 which will result in the distal ends (180 and 182) of the opposing digits maintaining an opposing pinch force.

FIG. 5 illustrates a movable digit 100 movably connected to a fixed digit 110 by a first connecting means 120. In this example, both the movable digit 100 and fixed digit 110 are manufactured from plastic. In the reduction to practice model the digit and pivot block parts are made from PVC sheet. Both a VO stop 540 and a VC stop 550 are manufactured from nylon. Stainless fasteners are used and the lever 140 is made from stainless steel. The tension cord 500 is made from a bungee cord. The first connecting means 120 consists of a stainless steel rivet and the movable digit 100 rotates around the rivet's axis, which extends orthogonal from the plane defined by the two digits (100 and 110).

The cable 510 in this prototype consists of an inelastic cord, for example Spectra® cord. The proximal end of the cable 510 is body-actuated by the user. The distal end 180 of the cable 510 passes through a cable guide 530 and is attached to the second end 144 of a lever 140. The cable guide 530 helps to maximize user efficiency by minimizing the body motion linear displacement needed to move the distal end 182 of the movable digit 100 a certain defined distance, as needed for a particular device and design. Fixing the cable 510 to move through this point establishes symmetry between the VONC modes and ensures the cable excursion starting positions are identical for both modes. This in turn, helps to minimize the length of cable 510 required. Alternatively, cord guide 530 may be absent and the cable 510 effectively held in the spatial position shown by a separate element external to the terminal device 200. A tension cord 500 is shown with one end of the tension cord 500, the proximal end, terminating at the second end 144 of the lever 140. In this prototype a hole is drilled through the second end 144 of the lever 140 and the tension cord 500 is passed through the hole and knotted to prevent the tension cord 500 from slipping back through the hole. The distal end of the tension cord 500 passes through a tension cord guide 520, in this case a hole drilled through the fixed digit 110, in the distal half of the fixed digit 110. Preferred embodiment will use a low-friction coefficient guide or a pulley to minimize drag on the tension cord 500 for more efficient operation. The tension cord 500 is passed through this hole and redirected back to the proximal end 185 of the fixed digit 110 were it is secured in place at the tension cord anchor 570. In this prototype, the tension cord 500 is simply passed through a tension cord anchor consisting of two holes drilled through the fixed digit 110, and tied off (not shown).

Referring again to FIG. 5, the first end 142 of the lever 140 is secured at a second connecting means 130, which in this prototype consist of a metal pin. Both the first and second connecting means (120 and 130) pass through an optional element referred to as the lever guide 560. In this embodiment of the invention, the lever guide 560 consists of a plastic monolith with a groove machined into it. The lever guide 560 is fixed securely to the movable digit 100, either by the tension force applied by the first connecting means 120, and/or by the use of a suitable adhesive applied to the opposing faces of the lever guide 560 and the movable digit 100. The second connecting means 130, a metal pin, is secured through a hole that has been drilled through the monolith, the first end 142 of the lever 140, and continues and terminates in the monolith. This hole for the second connecting means 130 is essentially perpendicular to the first connecting means 120, the rivet, and enables the lever 140 to be rotated around the pivot point created by the second connecting means 130, the pin, in a plane that is orthogonal to the plane created by the movable digit 100 and the fixed digit 110.

FIG. 5 illustrates the second end 144 of the lever 140 positioned towards the palmar side 240 of the terminal device 200, referred to above as the "first position."

Figure 6:
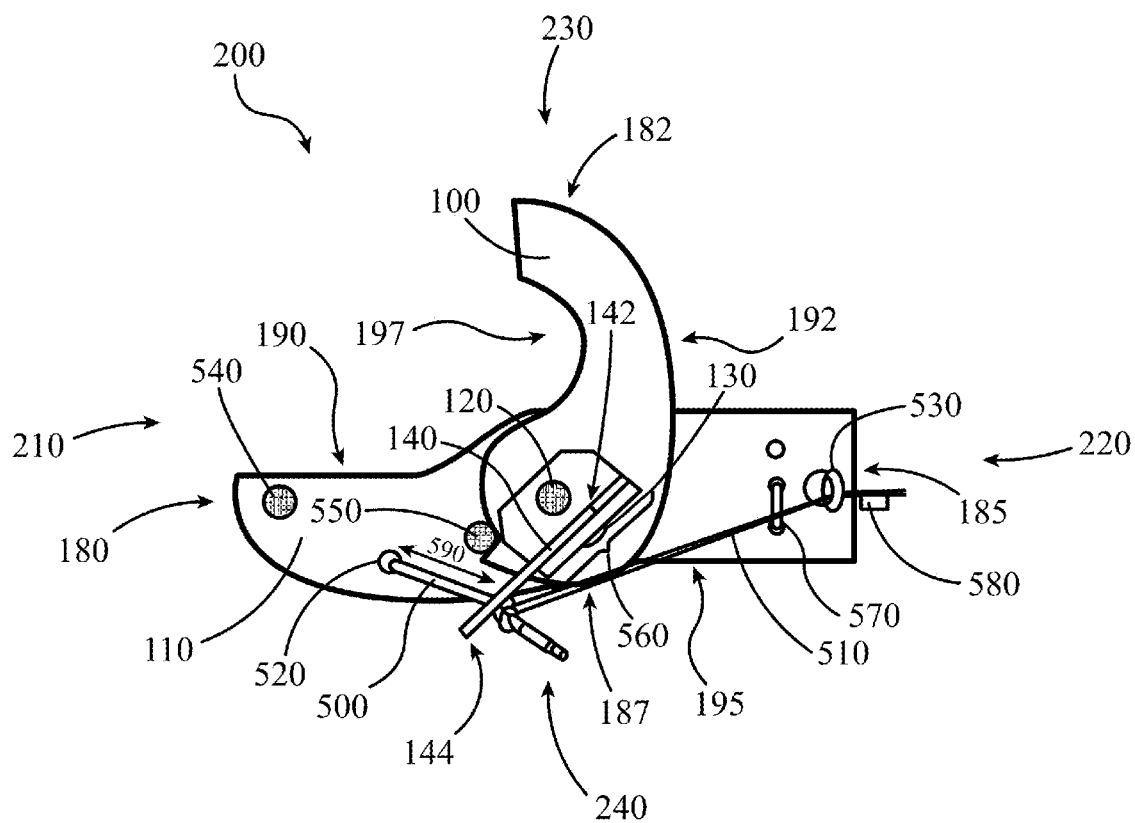
FIG. 6 illustrates an embodiment of the present invention, a reduction to practice of a switchable prehensor in voluntary closed mode, in the open position.

Referring to FIG. 6, the switchable terminal device 200 is shown in the open position, while still in the voluntary closed mode. Relative to FIG. 5, the user has released the force applying tension to the cable 530. The FLAG 580 located at the proximal end of the cable 510 illustrates the cable 510 starting position in the neutral state (for comparison to FIG. 7.) A second characteristic metric illustrated by FIG. 6, is LVC 590, the passive length of the tension cord 500, in the absence of an active force. This length, LVC 590, is one factor that defines the passive force applied by the tension cord 500 when the device is in voluntary close mode. FIG. 6 also illustrates that the amount of movement by the movable digit 100, or alternatively the degrees of arc that it opens or the swing angle, is controlled on the open end by the positioning of a VC stop 550.

Figure 7:
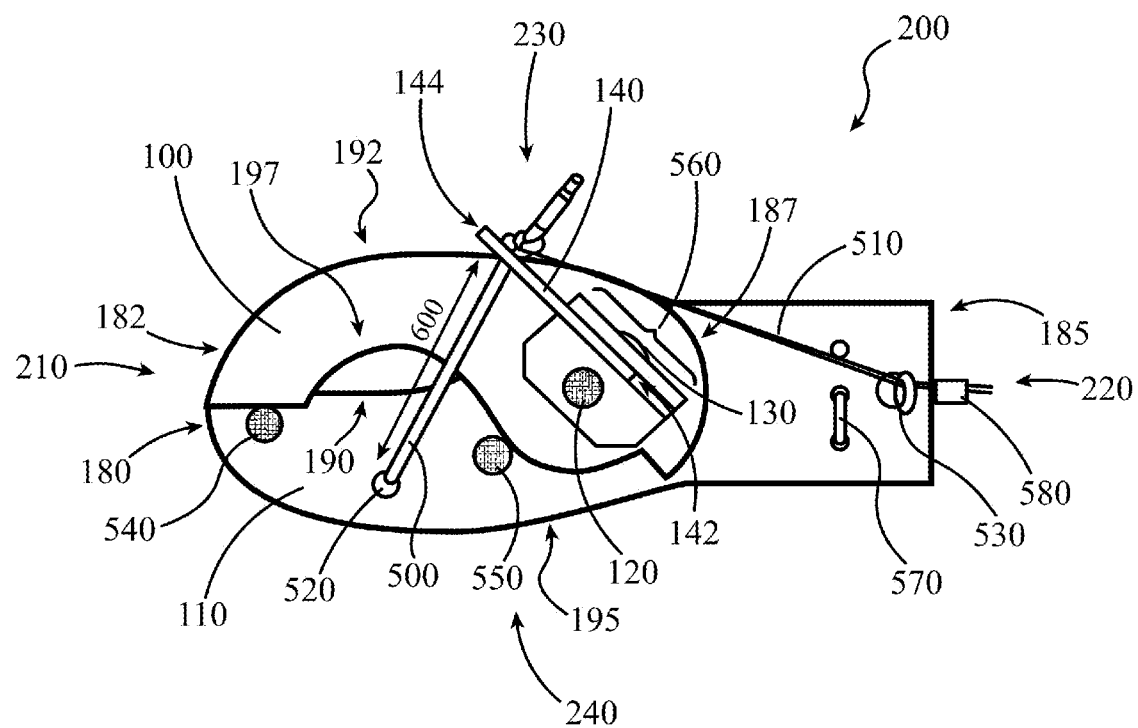
FIG. 7 illustrates an embodiment of the present invention, a reduction to practice of a switchable prehensor in voluntary open mode, in the closed position.

Referring now to FIG. 7, the switchable terminal device 200 is shown in the closed position, while in the voluntary open mode. The user has rotated the lever 140 around its pivot point, the second connecting means 130, from the first position (palmar) to the second position (dorsal) wherein the second end 144 of the lever 140 is oriented towards dorsal side 230 of the terminal device 200. The terminal device 200 remains in the passive state, wherein the user has not applied an actuating, active force to the cable 510. Note the position of the FLAG 580. It is identically positioned, as shown in FIG. 6 for the passive state while in the VC mode, right next to the cable guide 530. This illustrates that the objective of providing an easily switchable terminal device 200, wherein the cable 510 resting position is the same regardless of whether the terminal device 200 is in VO mode, or in VC mode, has been met. This is because of the careful selection of the geometric relationships between the fixed and movable digits 110, 100, the length of the lever 140 and the positioning of its second end 180 on the plane defined by the two digits (100 and 110) and relative to the point defined by the first connecting means 120.

FIG. 7 also illustrates the passive length of the tension cord 500, in the absence of an active force, that is LVO 600. Comparing this length for the passive state while in VO mode, to the length demonstrated in FIG. 6 for the passive state while in VC mode, it is clear that LVO 600 is much longer in FIG. 7 (in VO mode) than LVC 590 in FIG. 6. Since the tension cord 500 is an elastic band in this embodiment, the longer length for the tension cord 500 translates to a higher passive force applied to the lever 140, which means the active force that the user needs to apply to move the lever 140 to overcome this force is also higher.

Figure 8:
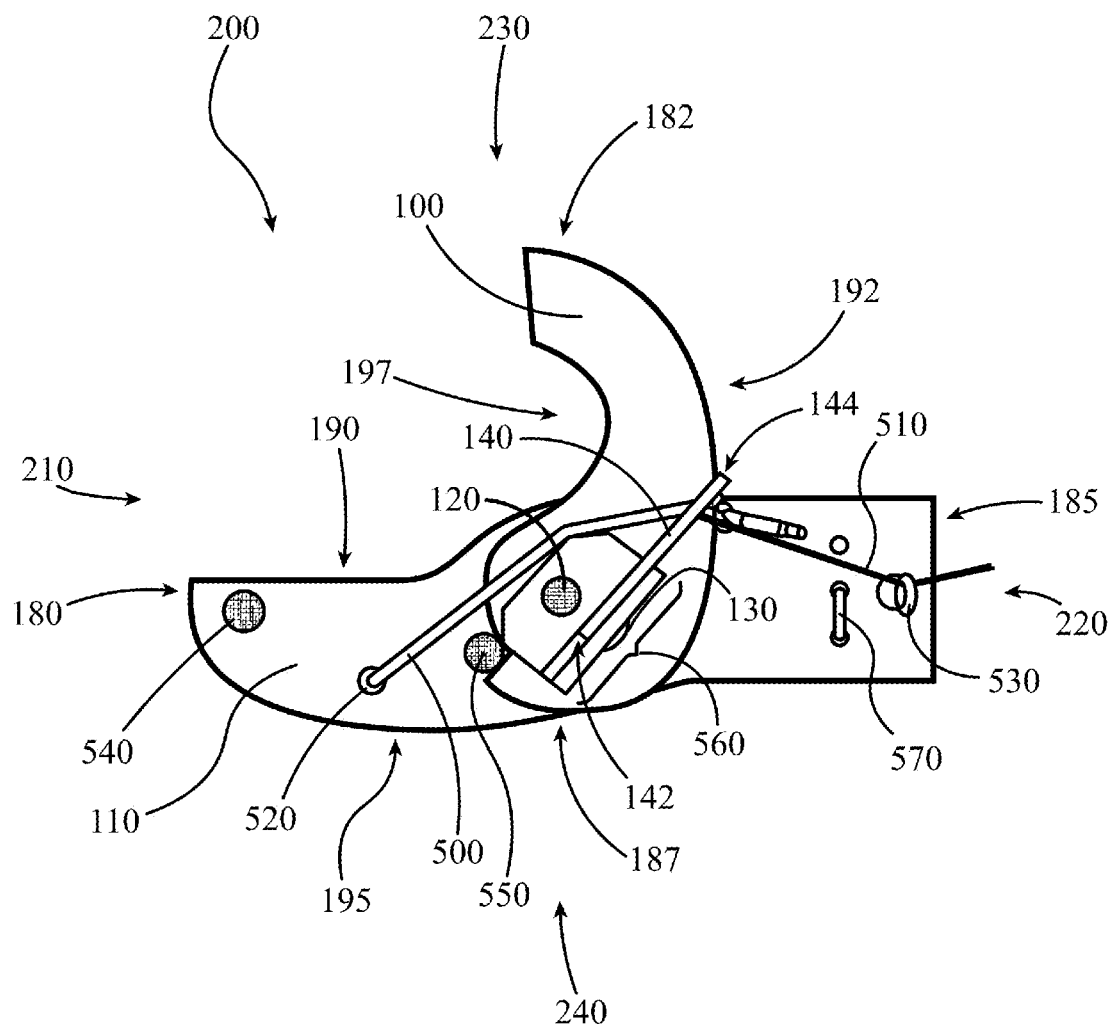
FIG. 8 illustrates an embodiment of the present invention, a reduction to practice of a switchable prehensor in voluntary open mode, in the open position.

FIG. 8 illustrates the prototype when the user has applied an active force greater than the passive force, by pulling the cable 510 in a proximal direction substantially parallel to the longitudinal axis of the fixed digit 110. In this case, the active force has pulled the second end 144 of the lever 140 from a distal position to a proximal position, in the process moving the distal end 182 of the movable digit 100 through a swing angle of about 90° until the movement is stopped by the VC stop 550. Releasing the active force and tension from the cable 510, will allow the passive force generated by the tension cord 500 to pull the second end 144 of the lever 140 back in the distal direction, such that the terminal device 200 returns to the passive closed position.

So, in summary, the passive force applied by the tension cord 500 while the terminal device 200 is closed during voluntary open mode is greater than the active force that the user needs to apply to move the terminal device 200 from open to closed while in voluntary closed mode. Thus, the objective of this disclosure to provide a switchable terminal device 200, wherein when the terminal device 200 is in VC mode, the force needed to open the terminal device 200 is relatively low, while still providing a comparably strong closing force when switched to the VO mode has been met.

What is claimed is:

1. A method of using a terminal device:
   mechanically connecting a first digit having a proximal end and a distal end positioned along an axis to a second digit having a distal end, such that the second digit can move relative to the first digit, wherein the movement of the second digit is substantially within a first plane, and the axis is positioned substantially within the first plane;
   mechanically connecting a first end of a lever to the second digit, the lever having a second end, such that the second end can move reversibly between a first position and a second position;
   applying a passive force to the second end in a first direction substantially towards the distal end of the first digit;
   applying an active force to the second end in a second direction substantially towards the proximal end of the first digit; and
   reversibly moving the second end in a second plane that is substantially perpendicular to the first plane from the first position to the second position and from the second position to the first position, wherein:
   when in the first position, the second end of the lever is oriented towards a palmar side of the terminal device relative to the axis,
   when in the second position, the second end of the lever is oriented towards a dorsal side of the terminal device relative to the axis,
   when in the first position and the applying the active force changes from a first active force that is less than the passive force to a first active force that is greater than the passive force, the lever rotates the second digit such that the terminal device switches from an open position to a closed position, and
   when in the second position and the applying the active force changes from a second active force that is less than the passive force to a second active force that is greater than the passive force, the lever rotates the second digit such that the terminal device switches from the closed position to the open position.

2. The method of claim 1, wherein the applying the passive force is performed using at least one of a spring, an elastic cord, or a pressurized cylinder.

3. The method of claim 1, wherein the applying the active force is performed using at least one of a cable, a rope, a cord, a fiber, a wire, or a filament.

4. The method of claim 1, wherein:
   the applying the passive force applies a first passive force when the second end is in the first position and the applying the active force applies an active force that is substantially equal to zero,
   the applying the passive force has a second passive force when the second end is in the second position and the applying the active force applies an active force that is substantially equal to zero, and
   a ratio of the first passive force to the second passive force is between 0.1 and 2.0, inclusively.

5. The method of claim 3, wherein:
   the applying the active force is performed by the cable, when the second end is in the first position and the applying the active force applies an active force that is substantially equal to zero, the cable defines a first cable resting position relative to the axis, and when the second end is in the second position and the applying the active force applies an active force that is substantially equal to zero, the cable defines a second cable resting position relative to the axis that is substantially equal to the first cable resting position.

6. The method of claim 4, wherein when the second end is in the second position and the applying the active force applies an active force substantially equal to zero, the applying the passive force applies a passive force between 2 $lb_f$ and 5 $lb_f$, inclusively.

7. The method of claim 1, wherein the reversibly moving rotates the distal end of the second digit between 30 degrees and 180 degrees relative to the distal end of the first digit.

* * * * *